United States Patent [19]

Thorengaard

[11] Patent Number: 4,870,196
[45] Date of Patent: Sep. 26, 1989

[54] METHOD OF PREPARING POWDERED, FREE-FLOWING TOCOPHERYL SUCCINATE

[75] Inventor: Bitten Thorengaard, Copenhagen, Denmark

[73] Assignee: Danochemo A/S, Ballerup, Denmark

[21] Appl. No.: 159,369

[22] PCT Filed: Jul. 8, 1987

[86] PCT No.: PCT/DK87/00086
§ 371 Date: Feb. 24, 1988
§ 102(e) Date: Feb. 24, 1988

[87] PCT Pub. No.: WO88/00045
PCT Pub. Date: Jan. 14, 1988

[30] Foreign Application Priority Data

Jul. 8, 1986 [DK] Denmark .............................. 3256/86

[51] Int. Cl.$^4$ .......................................... C07D 311/72
[52] U.S. Cl. .................................................. 549/410
[58] Field of Search ................................ 549/410, 413

[56] References Cited

U.S. PATENT DOCUMENTS 2,358,046  9/1944  Baxter et al. .......................... 549/410
3,551,457 12/1970  Ross ...................................... 549/410
4,002,706  1/1977  Pretorius ............................... 264/13

FOREIGN PATENT DOCUMENTS 1007161 10/1965 United Kingdom .

Primary Examiner—Nicky Chan
Attorney, Agent, or Firm—Watson, Cole, Grindle & Watson

[57] ABSTRACT

A method of preparing powdered, free-flowing tocopheryl succinate having a high bulk density comprising melting a mixture of tocopheryl succinate and wax, spraying the melt in a spraying zone containing a cloud of a powdering agent consisting of fine tocopheryl succinate and an additional powdering agent, and maintaining the product formed in a fluidized state by introducing cooling air until the tocopheryl succinate particles have hardened, and separating the product formed into a product fraction and a fine fraction, and recycling the fine fraction to the spraying zone.

14 Claims, 1 Drawing Sheet

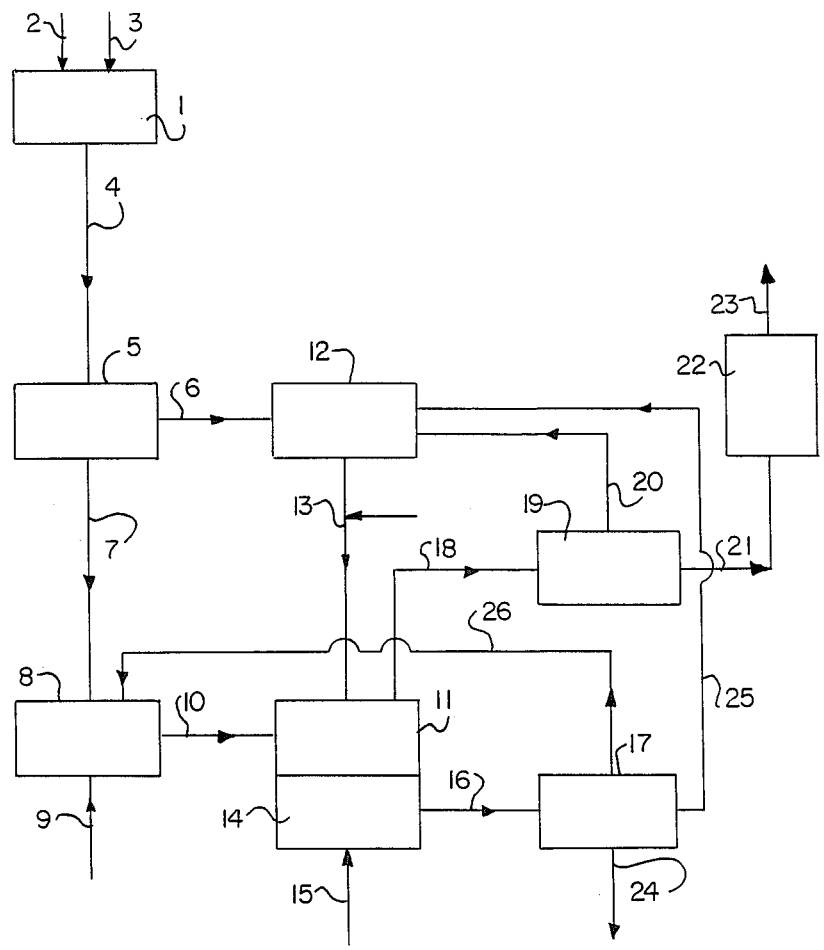

METHOD OF PREPARING POWDERED, FREE-FLOWING TOCOPHERYL SUCCINATE

The invention relates to a method of preparing powdered, free-flowing tocopheryl succinate having a high bulk density and wherein tocopheryl succinate is melted and the melt is sprayed so as to form droplets which are then cooled.

Tocopheryl succinate, which is a vitamin E, melts at 73°–78° C. It is a white solid material which at room temperature is greasy and tacky and which has poor flow properties. Furthermore, the commercially available tocopheryl succinate ordinarily has a broad particle size distribution with many fine particles which causes the powder to be cohesive and to form lumps. Therefore, it is difficult to formulate it into capsules and tablets having an exact content of the active compound in the methods normally employed for the formulation of vitamin preparations.

A number of attempts have been made to prepare free-flowing tocopheryl succinate with and without additives.

A prior art method is disclosed in U.S. Pat. No. 3,551,457. In this method tocopheryl succinate is heated to melt it, i.e., to about 85° C., and the melt is poured into a shallow pan so as to form a layer having a thickness of between 0.3 and 2.5 cm, after which the melt is allowed to harden and crystallize over a period of 12–24 hours. The resulting mass is then ground at a low temperature, preferably at a temperature of about −80° C. The prior art method is not suitable for commercial production because of the requirement of grinding at a very low temperature.

British Patent Specification No. 1,007,161 discloses another method of preparing free-flowing, powdered tocopheryl succinate having a high bulk density. In the method tocopheryl succinate is melted and the melt is dispersed in an aqueous solution containing a thickening agent in the form of methyl cellulose, and subsequently the dispersion formed is quickly cooled so as to cause the tocopheryl succinate to crystallize to form fine particles which are separated and dried.

A product thus prepared has a relatively broad particle size distribution which causes problems in the treatment of the product in known tabletting machines. Furthermore, the use of methyl cellulose as thickening agent results in a certain tackiness which imparts to the product a tendency to, adhere to e.g., parts of the tabletting machine.

Attempts to prepare tocopheryl succinate in the form of particles coated with other agents that the ones described above have not produced satisfactory results as these attempts have resulted in the reduction of the tocopheryl succinate content of the final product. This is undesirable because of the subsequent preparation of high-dosed capsules and tablets since for such use it is desirable that the starting material contains as much tocopheryl succinate as possible and that it also has a high bulk density.

The object of the invention is to provide free-flowing, powdered tocopheryl succinate which meets these requirements.

SUMMARY OF THE INVENTION

This object is obtained by the method according to the invention, which method is characterized in forming a melt of tocopheryl succinate and wax, spraying the melt in an spraying zone containing a cloud of a powdered agent in the form of fine tocopheryl succinate particles and an additional powdering agent, maintaining the resulting product in a fluidized state by supplying cooling air thereto for a sufficiently long period of time for the tocopheryl succinate particles to harden, separating the product formed into a product fraction and at least one fine fraction, and recycling the fine fraction to the spraying zone.

The invention is based on the discovery that by using fine tocopheryl succinate particles as powdering agent in the spraying of a tocopheryl succinate melt it is sufficient to use a relatively small amount of an additional powdering agent to obtain a final product having a high content of pure tocopheryl succinate. By separating the fine fraction from the hardened product the tendency displayed by the final product to act as a cohesive power and to form lumps is considerably reduced. As the separated fine fraction may be used as the powdering agent as mentioned above a double advantage is obtained by separating and recycling the fraction.

The use of wax in the tocopheryl succinate melt serves two purposes. Firstly, the wax increases the surface tension of molten tocopheryl succinate, which facilitates the formation of droplets during the spraying process of the melt in the spraying zone, and secondly the wax increases the hardening point of the melt so that the hardening takes place more quickly or at a higher temperature.

The latter effect is of particular importance as a pure tocopheryl succinate melt may be super-cooled down to temperatures as low as 0° C. or lower.

The type and amount of wax are preferably selected so as to cause the hardening point of the melt to be in the range of 15°–40° C. Examples of suitable waxes are Carnauba wax, Candelilla wax, and various other commercially available waxes, i.e., waxes sold under the trade names Lunacerin W 90, Lunacerin H 130, Hoechst E ph, Hoechst OM, Hoechst PE 190, Hoechst OP, Wax 722 V 28, and Bareco BE 195.

In a preferred embodiment an emulsifier, e.g., a fatty acid fraction, and optionally a white dye such as titanium dioxide is added to the melt of tocopheryl succinate and wax. The emulsifier serves to increase the bulk density of the final product and the white dye serves to improve the appearance of the product.

The additional powdering agent is preferably a silicate, aluminium oxide, calcium phosphate or magnesium stearate, and a particularly preferred powdering agent is finely divided $SiO_2$.

Examples of such commercially available products are Wacker HDK V15, Wacker HDK H2000, Degussa Sipernat 22 and Sipernat D17, Degussa Aerosil 200, Aerosil R 972, Cab-O-Sil, H-Sil T 600, Wacker HDK N 20, and Grace Syloid 74.

The two powdering agents settle on the tocopheryl succinate droplets as a thin layer so that particles of the product formed typically have a diameter of about 0.1–0.8 mm, preferably 0.125–0.595 mm.

The temperature in the spraying zone is preferably maintained at 0°–20° C. and more preferably is 0°–5° C. The coated droplets are preferably transferred directly into a fluid bed. The temperature of the cooling air serving to sustain the fluid bed is preferably approximately the same as in the spraying zone, i.e., 0°–20° C., preferably 0°–5° C. The coated hardened droplets are preferably maintained in a fluidized state for a period of 2–8 hours.

As mentioned above the resulting product is divided into at least two fractions, i.e., a product fraction and a fine fraction, the latter being recycled to the spraying zone.

Examination of the product fraction shows that it only contains a very small amount of the additional powdering agent. Thus when using a powdering agent containing about 5% $SiO_2$ the amount of finely divided $SiO_2$ in the product fraction is below 3%. The powdering agent is preferably used in an amount of 0.1–7% of the weight of the tocopheryl succinate. The fine material which is released during the fluidization is preferably separated from the air in a cyclone connected with the fluidization zone and the separated fine material is recycled from the cyclone to the spraying zone. Similarly, the fine fraction obtained by fractioning the product which removed from the fluid bed is recycled to the spraying zone.

Furthermore, it is preferred to separate a coarse fraction in connection with the fractioning of the product removed from the fluid bed and to recycle the coarse fraction to the melt of tocopheryl succinate and wax.

The fractioning is preferably effected in such a way that particles having a particle size below 125 μm and above 595 μm are separated so that the product fraction has a particle size between 125 and 595 μm.

A very high degree of dosage accuracy is obtained in the subsequent tabletting process by using a product having such a narrow particle size distribution.

BRIEF DESCRIPTION OF THE FIGURE

The invention will now be described with reference to the accompanying FIGURE which shows a flow diagram of the method according to the invention.

DETAILED DESCRIPTION OF INVENTION

In the FIG. 1 shows a mixer to which powdered, tocopheryl succinate and fine $SiO_2$ are fed through the pipes 2 and 3 respectively. The mixture obtained in the mixer 1 passes through a pipe 4 to a sieve 5 wherein the mixture is fractioned into a fraction consisting of particles having a small particle size and another fraction consisting of relatively coarse particles. The fine particles are removed through a pipe 6 and the coarse particles through a pipe 7 which is connected with a melting apparatus 8 to which a mixture of wax, emulsifier and white dye is fed through a pipe 9.

After being melted the mixture is introduced through a pipe 10 into a sprayer 11. The fine fraction is fed through the pipe 6 to a silo 12 and therefrom through a pipe 13 to the sprayer 11. At the same time cold air is introduced through the pipe 13. The fine material from the silo 12 is caused to form a cloud of solid particles in the sprayer 11 and the melt is sprayed in said cloud from the melting apparatus 8 in the form of droplets having a diameter of about 0.3 mm. During the concurrent cooling the droplets are coated with a thin layer of fine particles of tocopheryl succinate and $SiO_2$ and the material is fed directly to a fluidization zone 14 to which cold air is introduced through a pipe 15.

From the fluidization zone 14 particles are removed through a pipe 16 and the particles are fed to a sieve 17. A stream of particle-containing air is simultaneously removed from the top of the sprayer 11 through a pipe 18, the pipe communicating with a cyclone 19. From the cyclone 19 fine particles are removed through a pipe 20 and the particles are fed to the silo 12. At the same time particle-containing air is removed through a pipe 21 which communicates with a filter 22 serving to separate the remaining particles from the air which is then released to the surroundings through a pipe 23.

The product is divided into three fractions on the sieve 17, i.e., a product fraction which is removed through a pipe 24, a fraction consisting of fine particles which is removed through a pipe 25 and fed to the silo 12 through the pipe and a relatively coarse fraction which is fed to the melting apparatus through a pipe 26.

The invention will also be explained in further detail with reference to the following example:

EXAMPLE 1

A plant is employed having the construction corresponding to the one shown in the drawing.

A mixture of 10 kg tocopheryl succinate powder (1200 int. vitamin E units/g) and 500 g finely divided $SiO_2$ was prepared. The mixture was fractioned on a sieve into two fractions having an average particle size below and above about 350 μm. The relatively coarse fraction was fed into an electrically heated melting pot which was maintained at a temperature of about 92° C. 75 g Carnauba wax, 15 g emulsifier in the form of a fatty acid fraction and 15 g titanium dioxide were added to the melt. The fine fraction (7.5 kg) was transferred to a dosing silo for the below mentioned spraying tower. The melt (3 kg) was fed into a spraying tower with at a rate of 650 g/min. and sprayed therein in the form of droplets (about 0.3 mm) in a cloud of fine particles which at the same time were fed into the spraying tower from the silo in an amount of 1200 g/min. The spraying of the melt was effected by means of a disc sprayer.

The temperature in the spraying tower was 0°–5° C. and during the passage down through the tower a surface hardening of the tocopheryl succinate droplets took place. The product thus formed was then maintained in a fluidized state for about 4 hours by introducing cooling air having a temperature of 0°–5° C., which caused the tocopheryl succinate droplets to crystallize. The cooled product was then removed and sieved into three fractions, i.e., a product fraction having particle sizes of between 125 and 595 μm and a coarse and fine fraction. The fractions constituted 97%, 0.5%, 2.5% respectively of the cooled product. The product fraction constituted about 97% of the tocopheryl succinate supplied. A fine fraction separated in a cyclone and the fine fraction obtained by the sieving were recycled to the dosing silo and the coarse fraction obtained by the sieving was recycled to the melting pot.

The resulting final product was a free-flowing product having a high bulk density and a tocopheryl succinate content of 1150 int. vitamin E units/g which is equivalent to 95.8% of the vitamin E content of the starting material.

EXAMPLE 2

A plant was employed having a construction corresponding to the one shown in the drawing except that the additional powdering agent was fed into the silo 12 instead of into the mixer 1. An amount of 17 kg tocopheryl succinate powder (1200 int. vitamin E units) was used and it was fractioned on a sieve into two fractions having an average particle size below and above about 100 μm. The relatively coarse fraction (10.2 kg) was fed into an electrically heated melting pot which was maintained at a temperature of about 93° C. 255 g white bees's wax (Cera Alba), 51 g emulsifier in the form of a fatty acid fraction and 51 g titanium dioxide were added to the melt. The fine fraction was transferred to the dosing silo of the below mentioned spraying tower. 68 g fine $Al_2O_3$ was added to said tower followed by a mixing of the tocopheryl succinate and $Al_2O_3$ contained in the silo. The melt was introduced at a rate of 500 g/min. into the spraying tower and sprayed therein in the form of droplets (about 0.3 mm) in a cloud of fine particles which at the same time were introduced into the spraying tower from the silo in an amount of 1000 g/min. The spraying of the melt was effected by means of a disc sprayer. The temperature in the spraying tower was 0°–5° C. and during the passage down through the tower a surface hardening of the tocopheryl succinate droplets took place.

The product thus formed was then maintained in a fluidized state for about 4 hours by introducing cooling air of a temperature of 0°–5° C. causing the tocopheryl succinate droplets to crystallize. The cooled product was then removed and sieved into three fractions i.e. a product fraction having particle sizes of between 125 and 595 μm and a coarse fraction and a fine fraction. The product fraction constituted about 96.5% of the tocopheryl succinate used.

A fine fraction separated in a cyclone and the fine fraction from the sieving were recycled to the dosing silo and the coarse fraction from the sieving was recycled to the melting pot.

The resulting final product was a free-flowing product having a bulk density of 0.574 g/cm$^3$ and a tocopheryl content of 1146 int. vitamin E units/g which is equivalent to 95.5% of the vitamin E content of the starting material.

EXAMPLE 3

Another test was performed in a plant as described in example 2. 10 kg tocopheryl succinate powder (1200 int. vitamin E units) was used and it was fractioned on a sieve into two fractions having an average particle size below and above about 100 μm. The relatively coarse fraction (6 kg) was introduced into an electrically heated melting pot which was maintained at a temperature of about 93° C. 90 g Carnauba wax, 60 g emulsifier in the form of a fatty acid fraction and 30 g titanium dioxide were added.

The fine fraction (4 kg) was transferred to a dosing silo of the below mentioned spraying tower. 80 g fine $SiO_2$ was added after which the tocopheryl succinate and $SiO_2$ contained in the silo were mixed. The melt was introduced at a rate of 500 g/min into the spraying tower and sprayed therein in the form of droplets (about 0.3 mm) in a cloud of fine particles which at the same time were introduced into the spraying tower from the silo in an amount of 1000 g/min.

The spraying of the melt was effected by means of a disc sprayer. The temperature in the spraying tower was 0°–5° C. and during the passage down through the tower a surface hardening of the tocopheryl succinate droplets took place. The product thus formed was then maintained in a fluidized state for about 4 hours by introducing cooling air having a temperature of 0°–5° C. so as to cause the tocopheryl succinate droplets to crystallize. The cooled product was then removed and sieved to form three fractions, i.e., a product fraction having particle sizes of between 125 and 595 μm and a coarse fraction and a fine fraction. The product fraction constituted about 94.9% of the tocopheryl succinate used.

A fine fraction separated in a cyclone and the fine fraction (1.4%) obtained by the sieving were recycled to the dosing silo, and the coarse fraction obtained by the sieving (3.6%) was recycled to the melting pot.

The resulting final product was a free-flowing product having a bulk density of 0.551 g/cm$^3$ and a tocopheryl succinate content of 1130 int. vitamin E units/g which is equivalent to 94.2% of the vitamin E content of the starting material.

EXAMPLE 4

Another example was performed in a plant as described in example 2. 10 kg tocopheryl succinate powder (1200 int. vitamin E units) was used and it was fractioned on a sieve into two fractions having an average particle size below and above about 100 μm. The relatively coarse fraction (6 kg) was introduced into an electrically heated melting pot which was maintained at about 92° C. 180 g Carnauba wax was added to the melt.

The fine fraction (4 kg) was transferred to a dosing silo for the below mentioned spraying tower. 40 g fine $SiO_2$ was added after which the tocopheryl succinate and $SiO_2$ contained in the dosing silo were mixed. the melt was introduced at a rate of 500 g/min into the spraying tower and sprayed therein in the form of droplets (about 0.3 mm) in a cloud of fine particles which at the same time were introduced into the spraying tower from the silo in an amount of 1000 g/min.

The spraying of the melt was effected by means of a disc sprayer. The temperature in the spraying tower was 0°–5° C. and during the passage down the tower a surface hardening of the tocopheryl succinate droplets took place.

The product thus formed was then maintained in a fluidized state for about 4 hours by introducing cooling air having a temperature of 0°–5° C. so as to cause the tocopheryl succinate droplets to crystallize. The cooled product was then removed and sieved to form three fractions, i.e., a product fraction having particle sizes of between 125 and 595 μm and a coarse fraction and a fine fraction. The product fraction constituted about 95% of the tocopheryl succinate used.

A fine fraction separated in a cyclone and the fine fraction (1.7%) obtained by the sieving were recycled to the dosing silo, and the coarse fraction obtained by the sieving (3.3%) was recycled to the melting pot.

The resulting final product was a free-flowing product having a bulk density of 0.530 g/cm$^3$ and a tocopheryl succinate content of 1153 int. vitamin E units which is equivalent to 96.1% of the vitamin E content of the starting material.

COMPARATIVE EXAMPLE

Two products, A and B, prepared as described in the above mentioned example were compared with a commercially available product, C, which is sold under the name "Eastman, spec. grade" and which is assumed to be prepared as described in Canadian patent specification No. 691.951 (corresponding to British Patent Specification No. 1,007,161) and pure tocopheryl succinate, D. The comparison was effected by determining the tocopheryl succinate content of the four products, the bulk density and the flow properties, and the fluctuations in the weight of the tablets prepared from said products.

(1) Vitamin E content.

By using pure tocopheryl succinate as standard (=100% vitamin E) the vitamin E content of the three other products was determined.

The following results were obtained:

| Product | Vitamin E content compared with pure tocopheryl succinate (product D) |
|---|---|
| A | 95.7% |
| B | 94.2% |
| C | 98% |

Even though the products prepared according to the method of the invention have a lower potency than the known product, they are still high potency products.

(2) Bulk density.

The bulk density was determined partly in loose condition and partly after tapping on the wall of the measuring container.

The examination gave the following results:

| | Bulk density, g/cm$^3$ | |
|---|---|---|
| Product | Loose condition | After tapping |
| A | 0.546 | 0.619 |
| B | 0.537 | 0.610 |
| C | 0.557 | 0.650 |
| D | 0.447 | 0.601 |

As will appear from the table above, the bulk density of the products prepared according to the method of the invention is of the same order as that of the known product.

(3) Flow properties.

The slide angle of the products was determined concurrently with a visual evaluation of the flow properties. The examination gave the following results:

| Product | Slide angle | Visual evaluation of flow properties |
|---|---|---|
| A | 34° | free-flowing |
| B | 34° | free-flowing |
| C | 56° | non free-flowing |
| D | 90° | non free-flowing |

As will appear from the table above, the products prepared according to the method of the invention have much better flow properties than the other products.

(4) Weight deviation.

10 tablets were prepared from each product. The tablets had the following composition:

| Tococpheryl succinate | 400 mg |
|---|---|
| "Avicel" 101 | 100 mg |
| Lubricant | 10 mg |

The weight of the tablets formed was then determined and the following results were obtained:

| | Product | | | |
|---|---|---|---|---|
| | A | B | C | D |
| Weight, mg | 508.9 | 502.8 | 515.3 | 513.2 |
| | 506.0 | 506.1 | 508.8 | 515.4 |
| | 515.6 | 500.1 | 518.5 | 518.4 |
| | 509.3 | 504.9 | 519.9 | 507.0 |
| | 510.1 | 500.6 | 520.5 | 482.2 |
| | 507.3 | 504.7 | 515.2 | 509.4 |
| | 504.8 | 503.0 | 510.4 | 491.9 |
| | 506.9 | 500.9 | 490.6 | 514.2 |
| | 512.2 | 505.4 | 514.3 | 487.0 |
| | 509.1 | 504.2 | 518.4 | 518.9 |
| Average value | 509.0 | 503.3 | 513.2 | 505.8 |
| Standard deviation | 3.1 | 2.1 | 8.8 | 13.6 |
| Relative standard deviation | 0.62 | 0.43 | 1.72 | 2.69 |

As will appear from the table above a markedly improved uniformity is obtained with regard to the weight of the tablets by using a tocopheryl succinate product prepared according to the method of the invention.

I claim:

1. A method of preparing powdered, free-flowing tocopheryl succinate having a high bulk density wherein tocopheryl succinate is melted and the melt is sprayed so as to form droplets which are then cooled, comprising the steps of forming a melt of tocopheryl succinate and wax, spraying said melt in an spraying zone containing a cloud of a powdering agent in the form of particles of fine tocopheryl succinate and an additional powdering agent, maintaining the product thus formed in a fluidized state by supplying cooling air thereto for a sufficiently long period of time for the tocopheryl succinate particles to harden, separating the product formed into a product fraction and at least one fine fraction, and recycling the fine fraction to the spraying zone.

2. A method according to claim 1, wherein sufficient wax is utilized that the hardening point of the melt is in the range of 15°–40° C.

3. A method according to claim 1, wherein an emulsifier is added to the melt of tocopheryl succinate and wax.

4. A method according to claim 1, wherein a white dye is added to the melt of tocopheryl succinate and wax.

5. A method according to claim 1, wherein the melt is sprayed in the form of droplets having a diameter of 0.1–0.8 mm.

6. A method according to claim 1, wherein the additional powdering agent is finely divided SiO$_2$.

7. A method according to claim 6, wherein said finely divided SiO$_2$ is added in an amount of 0.1–7% of the weight of tocopheryl succinate.

8. A method according to claim 1, wherein the spraying of the melt is effected at a temperature of 0°–20°.

9. A method according to claim 1, wherein the hardened product is maintained in a fluidized state at a temperature between 0° and 20° C.

10. A method according to claim 9, wherein the hardened product is maintained in a fluidized state for 2–8 hours.

11. A method according to claim 1, wherein a coarse fraction is separated from the hardened product and is recycled and melted.

12. A method according to claim 5, wherein said droplets have a diameter of 0.125–0.595 mm.

13. A method according to claim 8, wherein said temperature is 0°–5° C.

14. A method according to claim 9, wherein said temperature is 0°–5° C.

* * * * *